United States Patent [19]

Khan et al.

[11] Patent Number: 5,302,385
[45] Date of Patent: Apr. 12, 1994

[54] POLYURETHANE-POLYVINYLPYRROLI-DONE BLOCK COPOLYMER AND IODINE CARRIER THEREFROM

[75] Inventors: Mohammad A. Khan, Sandy, Utah; Mutlu Karakelle; Min-Shiu Lee, both of Spring Valley, Ohio; Robert A. Taller, Centerville, Ohio

[73] Assignee: Becton, Dickinson and Company, Franklin Lakes, N.J.

[21] Appl. No.: 569,804

[22] Filed: Aug. 20, 1990

[51] Int. Cl.$^5$ .................. A61L 15/00; A61L 29/00
[52] U.S. Cl. ................... 424/486; 424/445; 525/326.9
[58] Field of Search ............... 525/326.9; 424/80, 486, 424/445

[56] References Cited

U.S. PATENT DOCUMENTS

| | | |
|---|---|---|
| 3,216,983 | 11/1965 | Shelanski et al. ............... 525/326.9 |
| 3,235,446 | 2/1966 | Shelanski et al. . |
| 4,254,239 | 3/1981 | Straub et al. ............... 525/326.9 |
| 4,373,009 | 2/1983 | Winn . |
| 4,381,380 | 4/1983 | LeVeen et al. . |
| 4,550,126 | 10/1985 | Lorenz ............... 521/159 |
| 4,642,267 | 2/1987 | Creasy et al. . |
| 4,692,328 | 9/1987 | Kitchell et al. ............... 424/80 |
| 4,769,013 | 9/1988 | Lorenz et al. . |

OTHER PUBLICATIONS

Schenck et al. *Journal of Pharmaceutical Sciences*, 68, 1505, 1979.

Primary Examiner—Thurman K. Page
Assistant Examiner—Peter F. Kulkosky
Attorney, Agent, or Firm—Richard E. Brown

[57] ABSTRACT

A copolymer having free hydroxyl groups is formed from N-vinyl pyrrolidone and allyl alcohol. A polyurethane is formed from a reaction mixture which includes the copolymer, a diisocyanate, a chain extender and a polyglycol. The polyurethane takes up iodine to give a complex useful as an antimicrobial coating on a medical article or as an antimicrobial foam sponge or wound dressing.

17 Claims, No Drawings

POLYURETHANE-POLYVINYLPYRROLIDONE BLOCK COPOLYMER AND IODINE CARRIER THEREFROM

BACKGROUND OF THE INVENTION

1. Field of the Invention

This invention relates to germicidal compositions, and more particularly relates to an iodine carrier having polyvinylpyrrolidone blocks in a polyurethane.

2. Background

Iodine is a well-known germicide with activity against a wide range of bacteria and viruses, and much effort has been directed to finding satisfactory vehicles for its administration. Some polymeric materials form complexes with iodine. These complexes, termed iodophors, are used commercially with a sponge or brush for germicidal cleaning or scrubbing. Often, such implements are included in a kit of materials which may also include other items useful for patient preparation, such as towels, gloves, nail cleaners and the like. Polyurethanes are disclosed as iodophors by Shelanski, U.S. Pat. No. 3,235,446 and by LaVeen in U.S. Pat. No. 4,381,380.

Another polymer well-known to form an iodophore is polyvinylpyrrolidone (PVP), and PVP iodophores have been extensively used as germicidal preparations. The structure of PVP-iodine is discussed by Schenck et al. in the *Journal of Pharmaceutical Sciences* 68, 1505 (1979).

A blend of PVP and polyurethane is applied to a substrate surface as a hydrophilic coating in U.S. Pat. No. 4,642,267 to Creasy et al. Creasy et al. is not concerned with iodine delivery.

A copolymer of PVP with a hydroxyethyl acrylate is disclosed by Winn in U.S. Pat. No. 4,373,009. The copolymer is applied as a lubricious coating to a substrate surface by first priming the surface with an isocyanate and then reacting the isocyanate with the copolymer. Winn et al. is also not concerned with iodine delivery.

Lorenz et al. in U.S. Pat. No. 4,769,013 discloses an interpenetrating polymer network complex of P-I and polyurethane which may be used in the form of a coating or foam.

Prior art iodophors used for iodine delivery suffer from various deficiencies such as instability leading to loss of iodine titer, tissue sensitivity due to the corrosive effects of iodine, and rapid water leachability of the iodophor.

While the above disclosures have improved the delivery of iodine, further improvements, particularly an iodine carrier which delivers the iodine slowly, is needed. The present disclosure is directed to fulfillment of this need.

SUMMARY OF THE INVENTION

A copolymer of N-vinylpyrrolidone (NVP) and a vinyl monomer has a free hydroxyl and/or amino group. The copolymer is reacted with a diisocyanate, polyglycol and a chain extender to give a polyurethane having PVP blocks in the polymer chain. The PVP blocks complex with iodine so that the polyurethane serves as an iodophor and may be used as an antimicrobial coating on a medical article or as an antimicrobial foam sponge or wound dressing. Preferred copolymers are the addition polymerization products of NVP and allyl alcohol.

Thus the invention includes a copolymer of PVP and a functionalized vinyl monomer which may serve as an iodophor. The copolymer may also become part of a polyurethane having PVP blocks in the polymer chain. The polyurethane of the invention combines the iodine complexing property of PVP with the excellent physical properties of polyurethane. The PVP, being covalently bonded in the polymer chain, does not leach out when contacted with water. Delivery of iodine is accordingly slower so that less iodine is needed in the iodophor. Because iodine delivery is slower, the levels of released iodine, while sufficient for antimicrobial activity, are lower than with polyurethane-PVP-iodine complexes of the prior art so that the danger of iodine toxicity is substantially eliminated.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

Polyurethanes are conventionally synthesized from a diisocyanate, a polyglycol and a chain extender. The polyglycol component may, for example, be a polyetherglycol, a polyester glycol, a hydroxy terminated polysiloxane, a fluorinated glycol or mixtures or block copolymers thereof.

The polyurethane of the invention may include these conventional components and also includes a PVP block in the polymer chain. The PV block is introduced by including in the polyglycol component a copolymer of PVP having free hydroxyl or amino groups. The PVP copolymer may be an addition copolymer of NVP with a vinyl monomer of structure I

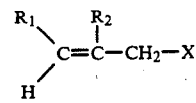

wherein $R_1$ and $R_2$ may be H or lower alkyl of 1 to 4 carbon atoms and X may be OH or $NH_2$. Preferred vinyl monomers are allyl alcohol and methallyl alcohol.

When the hydroxylated vinyl monomer is allyl alcohol, the addition polymer has the structure shown in II wherein m,n,o and p may independently be about 1 to 1,000, preferably about 1 to 50.

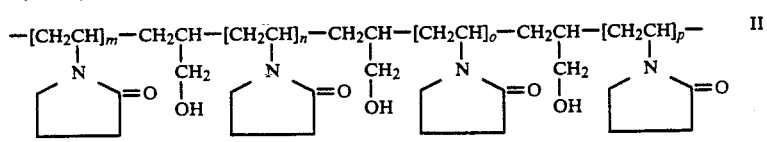

The addition polymerization of NVP and allyl alcohol may be carried out by conventional free radical procedures for copolymerizing vinyl monomers, and may be catalyzed by known free radical initiators such as azobisisobutyronitrile (AIBN) and peroxide. Details of the a suitable process are provided in Example I.

In copolymer II, the pendant pyrrolidone and hydroxymethylene groups are distributed along the chain in a ratio dependent on their proportion in the monomer mixture. Since allyl alcohol does not homopolymerize under the conditions of the copolymerization, the primary alcohol groups of the copolymer are randomly distributed along the polymer chain and have adjacent pyrrolidone groups. Copolymer II may contain from about 0.1 to 50, preferably about 10 to 15% of allyl alcohol.

Copolymer II forms a stable complex with iodine which may be used as an antimicrobial coating on an article or as a component of an antimicrobial surgical scrub. Preferably, copolymer II is used as a component of the polyurethane of the invention. The polyurethane may be synthesized from polyisocyanates, chain extenders and a polyglycol component which includes the hydroxy containing copolymer II.

Preferred polyisocyanates are diisocyanates. Suitable diisocyanates are aromatic diisocyanates such as 4,4-diphenylmethane diisocyanate (MDI) toluene diisocyanate (TDI) 3,3-diphenylmethane diisocyanate, alicyclic diisocyanates such as isophorone diisocyanate and 4,4'-dicyclohexylmethane diisocyanate, and aliphatic diisocyanates, as, for example, hexamethylene diisocyanate. The most preferred diisocyanates are MDI and TDI.

A conventional polyglycol component which may be used is a polyester glycol, a fluorinated glycol, a silicone glycol or preferably a polyether glycol or mixtures thereof. Suitable polyester glycols are, for example, polycaprolactone and polyethylene adipate. Suitable silicone glycols are, for example, polydimethylsiloxane glycols such as Q4 3667 available from Dow Corning Corp.

The preferred polyether glycol may be polyethyleneoxide glycol (PEG), polypropyleneoxide glycol or, polytetramethyleneoxide glycol (PTMEG). The most preferred glycols are PEG and PTMEG having a molecular weight of about 600 to 8,000 preferably about 1,000 to 3,000. These products are available commercially under the trade names Carbowax ® (Union Carbide Corp.) and Terathane ® (DuPont).

The chain extender may be water and/or a low molecular weight branched or unbranched diol, diamine or aminoalcohol of up to 10 carbon atoms or mixtures thereof. Representative nonlimiting examples of chain extenders are water; 1,4-butanediol (BDO); ethylene glycol; diethylene glycol; triethylene glycol; trimethylol propane; 1,2-propanediol; 1,3-propanediol; 1-6-hexanediol; 1,4-bis-hydroxymethyl cyclohexane, hydroquinone dihydroxyethyl ether, ethanolamine, ethylenediamine, hexamethylenediamine and 2-methyl-pentamethylene diamine. Preferred chain extenders are BDO and water.

Preferred polyurethanes of the invention may have a hard segment content of about 20 to 80, preferably about 30 to 50%. From the desired hard segment content, the proportion of isocyanate, polyglycol, chain extender and copolymer may readily be determined, and no further details with respect to ratio of the components is needed for a full understanding of the invention.

The polyurethane of the invention may be prepared by conventional bulk polymerization or solution polymerization techniques. As known in the art, a conventional polyurethane catalyst such as stannous octoate, may be used. For bulk polymerization, conventional polymerization equipment is charged with a mixture of the polyglycols, extender and catalyst in proportions predetermined in accordance with the desired hard segment-soft segment ratio. With vigorous stirring, the diisocyanate may be added all at once. If the reaction does not start spontaneously, the mixture may be heated sufficiently to induce an exothermic reaction. The reaction mixture may be stirred vigorously until the exotherm is complete and the temperature begins to drop off, generally for about 1 to 5 minutes. The clear homogeneous melt, while still hot, may advantageously be removed from the reactor prior to curing. In an alternative procedure, the polyglycols and diisocyanate may be mixed and, when the initial exotherm begins to subside, the extender may be added with continued stirring.

In solution polymerization, the polyglycols and extender may be mixed in a suitable solvent such as dimethylacetamide (DMAC) and a solution of the stoichiometric amount of diisocyanate in the same solvent added dropwise. After addition, the mixture may be heated with stirring to complete the polymerization. Example II provides details of a typical procedure.

Complexation with iodine may be accomplished merely by steeping the copolymer or polyurethane of the invention in an alcoholic solution of iodine whereby the iodine complexes with the PVP blocks in the polymer chains. In an alternative procedure for synthesis of the polyurethane iodine complex, the copolymer-iodine complex may be used in the polyurethane synthesis.

The polyurethane iodine complex may be used as a foam prepared by conventional foam technology using water as the chain extender. For this application copolymer II may be reacted with iodine, preferably by steeping in an alcoholic solution, to cause the PVP of the copolymer and iodine to complex. The polyglycol, water and a catalyst may then be mixed thoroughly with the complex, followed by addition of the isocyanate. The isocyanate reacts with the hydroxyl groups to give urethane linkages and with the water to give carbon dioxide The carbon dioxide serves as a blowing agent causing the polymeric mass to foam. This procedure is described in detail in Example IV.

As is conventional in the foam art, a stabilizer may be included in the foam preparation of the invention. Preferred stabilizers are silicones which reduce surface tension thereby providing uniformity in the size of the foam cells and protection against collapse of the cell walls. The concentration of stabilizer may be about 0.1 to 3.0% by weight of the foam.

The foam slab may be cut into any desired shape for use as an antimicrobial wound dressing, catheter cuff or preferably as a sponge. When brought into contact with water or a body fluid, the iodine is slowly released from the foam and provides a barrier against growth or migration of microorganisms.

In a preferred application, the polyurethane-iodine complex may be applied as an antimicrobial coating on a medical device wherein the release of iodine is sufficient to prevent infection (about 2 to 5 parts per million) but is slow enough to maintain the iodine concentration below the level of iodine toxicity during an extended catheterization procedure (often up to two weeks for urinary catheterization). Thus, the most preferred coating application is on a urinary catheter. In a typical coating procedure, the catheter may be dipped into a solution of the complex in a suitable solvent, such as dimethylacetamide (DMAC). The catheter may be of any polymer used conventionally for catheter fabrication, such as polyurethane, polyvinyl chloride and the like. The nature of the catheter to be dip coated with the polyurethane-iodine complex of the invention is not an aspect of the invention.

The following examples are provided to further describe the invention but are not to be considered as limitative of the invention.

EXPERIMENTAL

Materials

NVP was received from Aldrich Chemical Co. and vacuum distilled before use. Allyl alcohol, toluene and DMAC were obtained from Aldrich and used as received. AIBN was received from Polysciences Inc. and was used as received. PEG having a molecular weight of 1000 was obtained from Union Carbide Corp. and used as received. The determination of hydroxyl number by phthalic anhydride pyridine method and water content by Karl Fisher titration were performed to verify and adjust formulation stoichiometry. BDO was used as chain extender, as received, from DuPont. MDI was received from Mobay and was filtered and vacuum stripped before use.

EXAMPLE I

Copolymer of PVP and Allyl Alcohol

NVP and toluene were placed in a three-necked round bottom flask equipped with a magnetic stirrer, a condenser, a drying tube, a thermometer and an additional funnel. The mixture was degassed at 85° for 30 minutes by purging with dry nitrogen gas. The allyl alcohol was then added and a 5 ml sample was taken for GC analysis to follow the disappearance of allyl alcohol. Approximately 40% of the AIBN solution was added in one slug and the temperature was held at 85° C. The rest of the AIBN solution was added dropwise over 4 hours and the polymerization reaction was continued at 85° C. for one more hour. At this point, another 5 ml solution sample was taken for GC analysis. The toluene was then removed by steam distillation. Water content of the aqueous PVP-AA copolymer solution was reduced to approximately 30%. The concentrated aqueous polymer solution was placed on glass plates, air dried, and then vacuum dried at 50° C.

EXAMPLE II

Solution Synthesis of Polyurethane

Solution polymerization at 25% total solids was performed in DMAC under a nitrogen atmosphere. The hydroxyl functional copolymer from Example I and PEG were dried at 60° to 70° C under vacuum (4 to 6 mm Hg) for 4 to 6 hours to remove moisture. Stoichiometric amounts of the copolymer PEG and BDO were placed in the polymerization vessel and degassed at 60° C. for 30 minutes. Two thirds of the total DMAC was added to the polyol-extender mixture and the mixture was degassed for an additional 15 minutes. The stoichiometric (1.02 Index) amount of MDI was dissolved in the remaining DMAC and the solution was added dropwise to the polymerization vessel. The polymerization medium was maintained at 60° to 70° C. and constantly stirred. A polymerization time of four hours at 60° to 70° C. was sufficient for adequate polymer formation. If desired, the polymer may be isolated by pouring into water with stirring, filtering the precipitated polymer, washing and drying.

EXAMPLE III

Catheter Dip Coating

A polyvinyl chloride catheter was dipped into the DMAC solution of polyurethane of Example II, withdrawn and the DMAC removed by evaporation. The coated catheter was then dipped into an aqueous alcoholic solution of iodine or triiodide to cause complexation of iodine with the PVP blocks in the polyurethane coating.

EXAMPLE IV

Preparation of Polyurethane-Iodine Complex Foam

The copolymer of Example I was dry mixed with iodine (10% by weight) at 60° C. for 24 hours. Polyurethane foam was prepared using Hypol 2002 (W. R. Grace & Co., Lexington, Mass.) hydrophilic prepolymer. Three parts (by weight) of the dry iodine complex was dissolved in 25 parts of distilled water and the solution added to 30 parts of Hypol 2002 hydrophilic prepolymer in a mold cup. The mixture was stirred vigorously until the onset of the foaming process. The foam curing process was continued for two hours at ambient conditions. The skin of the foam complex was removed and the desired sizes of sponges cut from the slab foam.

What is claimed is:

1. A polymer comprising a block of polyurethane covalently bonded to a block of a copolymer of N-vinylpyrrolidone and allyl alcohol, said polyurethane comprising the reaction product of a diisocyanate, a polyglycol, and a chain extender.

2. The polymer of claim 1 wherein said diisocyanate is selected from the group consisting of 4,4'-diphenylmethane diisocyanate, 3,3'-diphenyl methanediisocyanate, 2,4-toluene diisocyanate, 2,6-toluene diisocyanate, isophorone diisocyanate, 4,4'-dicyclohexylmethane diisocyanate, hexamethylene diisocyanate and a mixture thereof.

3. The polymer of claim 1 wherein said polyglycol is selected from the group consisting of a polyether glycol, polyester glycol, silicone glycol, fluorinated glycol and a mixture thereof.

4. The polymer of claim 1 wherein said chain extender is selected from the group consisting of water, butanediol, ethylene glycol, diethylene glycol; triethylene glycol; 1,2-propanediol; 1,3-propanediol; 1-6-hexanediol; trimethylol propane, 1,4-bis-hydroxymethyl cyclohexane, hydroquinone dihydroxyethyl ether, ethanolamine, ethylenediamine, hexamethylenediamine and 2-methyl-pentamethylene diamine.

5. The polymer of claim 1 further comprising iodine complexed therewith.

6. The polymer of claim 1 in the form of a coating on a medical article.

7. The polymer of claim 6 wherein said medical article is a catheter.

8. The polymer of claim 1 in the form of a foam.

9. The polymer of claim 8 wherein said foam is a sponge.

10. The polymer of claim 8 wherein said foam is a wound dressing.

11. A polymer comprising a block of polyurethane covalently bonded to a block of a copolymer of N-vinylpyrrolidone and a vinyl monomer having a functional group selected from the group consisting of a hydroxyl group and an amino group, said polyurethane comprising the reaction product of a polyisocyanate, polyglycol, and chain extender.

12. The polymer of claim 11 further comprising iodine complexed therewith.

13. The polymer of claim 12 in the form of a coating.

14. The polymer of claim 12 in the form of a foam.

15. A polymer comprising a block of polyurethane covalently bonded to a block of a copolymer of N-vinylpyrrolidone and allyl alcohol, said polyurethane comprising the reaction product of a diisocyanate, a polyetherglycol, and a diol chain extender.

16. The polymer of claim 15 further comprising iodine complexed therewith.

17. The polymer of claim 16 in the form of a coating on a medical article.

* * * * *